United States Patent [19]
Hrib

[11] Patent Number: 5,880,121
[45] Date of Patent: *Mar. 9, 1999

[54] 4,5-DIHYDRONAPHTH (1,2-C) ISOXAZOLES AND DERIVATIVES THEREOF

[75] Inventor: Nicholas J. Hrib, Somerville, N.J.

[73] Assignee: Hoechst Marion Roussel Inc., Kansas City, Mo.

[*] Notice: This patent issued on a continued prosecution application filed under 37 CFR 1.53(d), and is subject to the twenty year patent term provisions of 35 U.S.C. 154(a)(2).

[21] Appl. No.: 769,343

[22] Filed: Dec. 19, 1996

Related U.S. Application Data

[60] Provisional application No. 60/069,890 Jan. 5, 1996.

[51] Int. Cl.[6] .......................... A61K 31/55; C07D 413/04
[52] U.S. Cl. .......................... 514/218; 514/255; 514/299; 514/305; 514/304; 514/321; 514/322; 514/379; 540/575; 544/368; 546/137; 546/183; 546/198; 546/199; 548/241
[58] Field of Search .......................... 548/241; 546/137, 546/183, 198, 199; 544/368; 540/575; 514/379, 304, 305, 299, 321, 322, 255, 218

[56] References Cited

U.S. PATENT DOCUMENTS

| | | | |
|---|---|---|---|
| 4,695,578 | 9/1987 | Coates et al. ........................... | 514/397 |
| 4,859,683 | 8/1989 | Youssefyeh et al. .................. | 514/299 |
| 4,886,808 | 12/1989 | King ....................................... | 514/299 |
| 5,371,087 | 12/1994 | Hrib et al. ............................ | 514/252 |
| 5,440,048 | 8/1995 | Ong et al. .............................. | 548/481 |

FOREIGN PATENT DOCUMENTS

| | | |
|---|---|---|
| 2119977 | 12/1971 | European Pat. Off. . |
| 0402644 | 12/1990 | European Pat. Off. . |
| 9410162 | 5/1994 | WIPO . |
| 9507893 | 3/1995 | WIPO . |

OTHER PUBLICATIONS

Sami et al., *Org. Prep. Proced. Int.*, vol. 23, No. 2, 1991, pp. 186–188.
Oldfson et al., *J. Org. Chem.*, vol. 49, No. 14, 1984, pp. 2652–2653.
Hashem et al., *J. Med. Chem.*, vol. 19, No. 2, 1976, pp. 229–239.
Taylor et al., *Tetrahedron*, vol. 23, No. 5, 1967, pp. 2081–2093.
Chem Abst. 114:247186, Sami et al., 1991.
Chem Abst. 101:37920, Olofson et al., 1984.
Kilpatrick, G.J. et al., *Medicinal Research Review*, vol. 10, No. 4 (1990) pp. 441–475.
Adembri,di G. et al., *Bull Sci Fac Chim Ind.* Bologna, 23 (1965) pp. 203–222.
Barber, G.N. et al. *J. Org. Chem.*, vol. 43, No. 15 (1978) pp. 3015–3021.
Stevens, R.V. et al., *Tetrahedron Letters*, vol. 25, No. 41 (1984) pp. 4587–4590.
Griffiths, J.S. et al., *J. Chem Soc.*, (C), (1971), pp. 947–975.
Carr, J.B. *Journal of Medicinal Chem.*, vol. 20, No. 7, (1977) pp. 934–939.
Costall, B. et al., *Pharma Ther.*, vol. 47 (1990) pp. 181–201.

*Primary Examiner*—Joseph K. McKane
*Attorney, Agent, or Firm*—Frommer Lawrence & Haug LLP

[57] ABSTRACT

4,5-Dihydronaphth[1,2-c]isoxazole derivatives of the general formula:

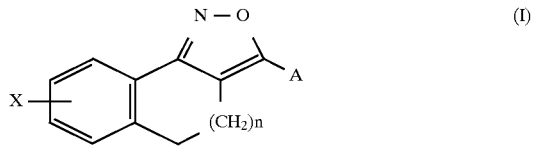

where A, X and n are defined herein are disclosed. Such compounds are useful as serotonin 5-HT$_3$ antagonists. These compounds art useful for the treatment of anxiety, psychiatric disorders, nausea, vomiting and drug dependency.

41 Claims, No Drawings

4,5-DIHYDRONAPHTH (1,2-C) ISOXAZOLES AND DERIVATIVES THEREOF

This application claims the benefit of Provisional Application 60/069,890 Jan. 5, 1996.

The present invention is directed to certain novel compounds and their use as pharmaceutical agents having unique central nervous system activity.

This invention relates to 4,5-dihydronaphth[1,2-c] isoxazoles and derivatives thereof, and their use as serotonin 5-HT$_3$ antagonists, which may be useful for the treatment of anxiety, psychiatric disorders, schizophrenia, nausea, vomiting and the control of drug dependency, of general formula (I):

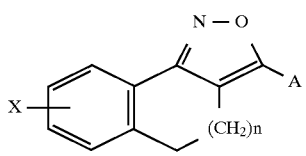

wherein A is hydrogen, hydroxy,

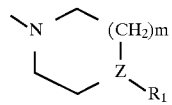

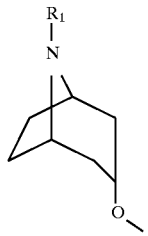

or

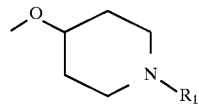

wherein
R$_1$ is hydrogen, an alkyl group of 1 to 6 carbons, optionally substituted with hydroxy, alkoxy or amino substitution; aryl or heteroaryl, optionally substituted with halogen, hydroxy or alkoxy; or benzyl optionally substituted with halogen, hydroxy or alkoxy;
n is an integer of 1 or 2;
Z is nitrogen, CH or C(OH);
m is an integer of 1 to 3; and
X is hydrogen, hydroxy or alkoxy;
or a pharmaceutically acceptable additional salt thereof, or where applicable, a geometric or optical isomer or racemic mixture thereof.

The present invention also relates to a process for preparing these compounds, pharmaceutically acceptable addition salts thereof, as well as the pharmaceutical acceptable compositions thereof, and a method of using the compounds as seroton 5-HT$_3$ antagonists.

Throughout the specification and appended claims, a given chemical formula or name shall encompass all stereo and optical isomers where such isomers exist. Additionally, a given chemical formula or name shall encompass the pharmaceutically acceptable additional salts thereof.

In a preferred embodiment of the invention are compounds of formula (I) wherein
A is

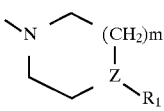

wherein
R$_1$ is hydrogen, an alkyl group of 1 to 6 carbons, optionally substituted with hydroxy, alkoxy or amino substitution; aryl or heteroaryl, optionally substituted with halogen, hydroxy or alkoxy; or benzyl optionally substituted with halogen, hydroxy or alkoxy;
n is an integer of 1 or 2;
Z is nitrogen;
m is an integer of 1 to 3; and
X is hydrogen, hydroxy or alkoxy.

More preferred, are compounds of formula (I) wherein
R$_1$ is hydrogen, or an alkyl group of 1 to 3 carbons;
n is 1;
Z is nitrogen;
m is 1 or 2; and
X is hydrogen.

The novel compounds of the present invention and the intermediates thereto may be prepared by the reaction sequence illustrated hereinbelow. The substituents Z, m, n and X are generally as defined above unless otherwise indicated.

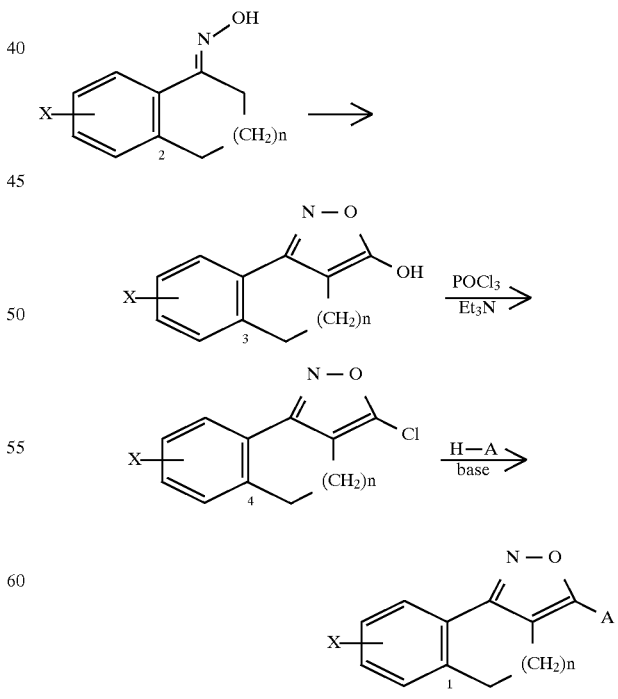

According to the preparation scheme, hydroxyisoxazoles 3 are prepared from oximes 2 in a solvent such as tetrahydrofuran (THF) at a temperature of from about 25° C. to about reflux temperature of the solvent for a period of from about 0.25 to about 4 hours according to the methods of Griffiths and Olofson (Jerome S. Griffiths, et al., J. Chem. Soc. C, 974 (1971) and G. N. Barber and R. A. Olofson, J. Org. Chem. 43, 3015 (1978)). The hydroxyisoxazoles 3 are converted to chloroisoxazoles 4 via treatment with phosphorous oxychloride in the presence of a suitable base, such as triethylamine, at a temperature of from about 100° to about 200° C. for a period of from about 0.25 to about 4 hours in a manner similar to that utilized by Adembri et al. (G. Adembri and P. Tedeschi, Bull. Sci. Fac. Chim. Ind. Bologna 23, 203 (1965)). Intermediates 4 are treated with an appropriate nucleophile H—A (wherein A is defined hereinbefore) at a temperature of from about 100° to about 200° C. with or without added base in an appropriate solvent, such as N-methylpyrrolidinone, to provide the novel compounds 1 of the invention.

These compounds may be prepared by the following representative examples. The examples are exemplary and should is not be construed as limiting the invention disclosed herein.

EXAMPLE 1

3-Chloro-4, 5-dihydronaphth[1, 2-c]isoxazole

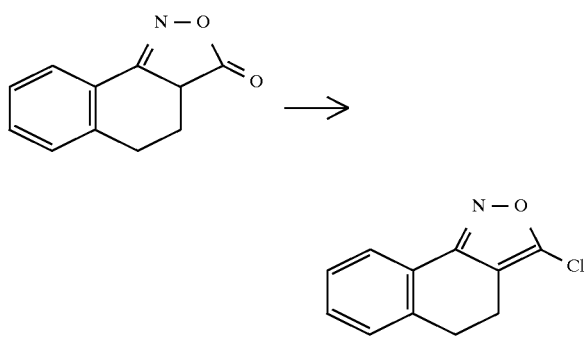

To a stirred mixture of 4,5-dihydronaphth[1,2-c]isoxazol-3-(3aH)-one (7.25 g, 38.77 mmol) in phosphorus oxychloride (10.84 ml, 116.3 mmol), triethylamine (5.40 ml, 38.77 mmol) was added dropwise. After completion of addition, the mixture was heated to reflux while stirring. After 2 hours, no starting material remained as shown by TLC [silica, ethylacetate (EtOAc)]. The mixture was cooled to room temperature, poured into 300 ml of ice water, and extracted with $CH_2Cl_2$. The organic extracts were combined, dried over $MgSO_4$ and concentrated in vacuo. The resultant solid was filtered through silica using $CH_2Cl_2$ eluent to provide 6.2 g of crude product. This crude product was recrystallized from a minimum of heptane to provide a product as needles, mp of 57°–59° C., homogeneous by thin layer chromatography (TLC) [silica, $CH_2Cl_2$, $R_f$=0.80]. The Infrared (IR) ($CHCl_3$), nuclear magnetic resonance (NMR) ($CDCl_3$), and Mass Spectrum ($M^+$=205, EI, 70 eV) were consistent with the structure. The yield was 5.417 g (26.4 mmol, 68.16%).

Elemental Analysis

|   | Calculated | Found |
|---|---|---|
| C | 64.25 | 64.02 |
| H | 3.92 | 3.86 |
| Cl | 17.24 | |
| N | 6.81 | 6.77 |
| O | 7.78 | |

EXAMPLE 2

3-(4-Methyl-1-piperazinyl)-4,5-dihydronaphth[1,2-c]isoxazole

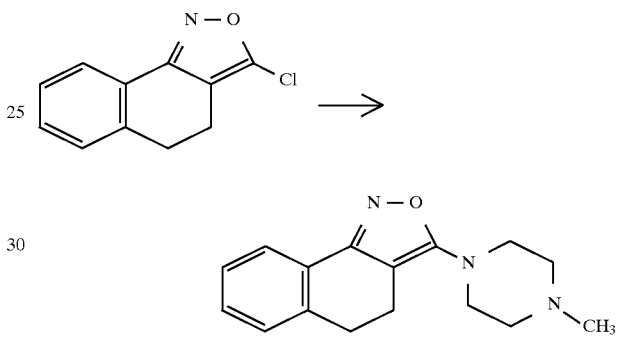

A stirred mixture of 3-chloro-4,5-dihydronaphth[1,2-c]isoxazole (2.65 g, 12.93 mmol), N-methyl piperazine (30 ml, 270.4 mmol) and $K_2CO_3$ (3.57 g, 25.87 mmol) under $N_2$ was lowered into an oil bath preheated to 150° C. The mixture was heated while stirring under $N_2$ for 2 hours. At that time, TLC [$CH_2Cl_2$] showed no remaining starting material. The mixture was removed from the heating bath and allowed to cool to room temperature. It was then partitioned between heptane/$H_2O$. The heptane phase was washed with water, dried over $MgSO_4$, filtered and concentrated in vacuo to yield a solid. This crude product was recrystallized from heptane/ether ($Et_2O$) to provide the product as needles, mp of 92°–94° C., homogeneous by TLC [silica, 1:1 $CH_3OH$:EtOAc, $R_f$=0.39]. The IR ($CHCl_3$), NMR ($CDCl_3$) and Mass Spectrum ($M^+$=269, EI, 70 eV) were consistent with the structure. The yield was 1.2555 g (4.67 mmol, 36.09%).

Elemental Analysis

|   | Calculated | Found |
|---|---|---|
| C | 71.35 | 71.34 |
| H | 7.11 | 6.98 |
| N | 15.60 | 15.78 |
| O | 5.94 | |

EXAMPLE 3

3-(4-(2-Hydroxyethyl)-1-piperazinyl)-4,5-dihydronaphth[1,2-c]isoxazole

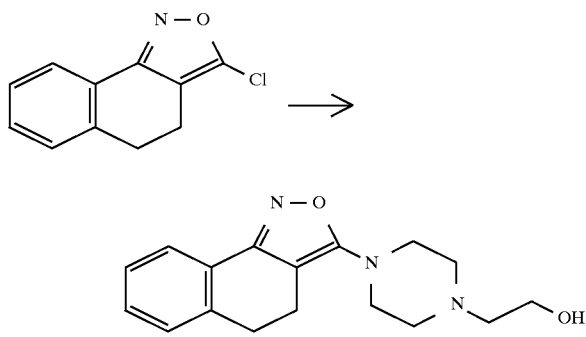

A stirred mixture of 3-chloro-4,5-dihydronaphth[1,2-c] isoxazole (3.0 g, 14.63 mmol), 1-(2-hydroxyethyl)-piperazine (17.95 ml, 146.3 mmol) and $K_2O_3$ (4.1 g, 29.3 mmol) in 18 ml of N-methylpyrrolidinone under $N_2$ was lowered into an oil bath preheated to 150° C. The mixture was heated while stirring under $N_2$ for 1 hour. At that time, TLC ($CH_2Cl_2$) showed no remaining starting material. The mixture was removed from the heating bath, allowed to cool to room temperature, and diluted with $H_2O$. Upon the addition of heptane, a solid precipitated. The solid was collected, washed with heptane and $H_2O$, and dried in vacuo (0.1 mm) at 85° C. overnight to provide pure product, mp of 137°–138° C., homogeneous by TLC [silica, 1:1 $CH_3OH$:EtOAc, Rf=0.67]. The IR ($CHCl_3$), NMR ($CDCl_3$) and Mass Spectrum ($M^+$=299, EI, 70 eV) were consistent with the structure. The yield was 2.603 g (8.70 mmol, 59.47%).

Elemental Analysis

|   | Calculated | Found |
|---|------------|-------|
| C | 68.21 | 68.12 |
| H | 7.07 | 7.01 |
| N | 14.04 | 14.14 |
| O | 10.69 | |

EXAMPLE 4

3-(1-Homopiperazinyl)-4,5-dihydronaphth[1,2-c]isoxazole

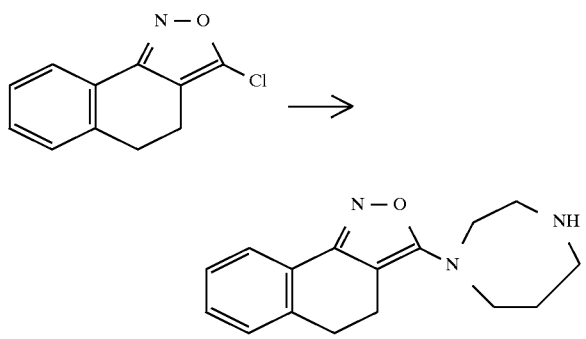

A stirred mixture of 3-chloro-4,5-dihydronaphth[1,2-c] isoxazole (3.0 g, 14.63 mmol) homopiperazine (14.66 g, 146.3 mmol) and $K_2CO_3$ (4.04 g, 29.3 mmol) in 16 ml of N-methylpyrrolidinone under $N_2$ was lowered into an oil bath preheated to 150° C. The mixture was heated while stirring under $N_2$ for 45 minutes. At that time, TLC ($CH_2Cl_2$) showed no remaining starting material. The mixture was removed from the heating bath, allowed to cool to room temperature, diluted with $H_2O$ and extracted with $Et_2O$. The $Et_2O$ phase was dried over $MgSO_4$, filtered and concentrated in vacuo. The crude solid obtained was recrystallized from heptane/$Et_2O$ and dried in vacuo (0.1 mm) at 85° C. overnight to provide pure product, mp of 79°–81° C., homogeneous by TLC [silica, 1:1 $CH_3OH$:EtOAc, Rf=0.17]. The IR ($CHCl_3$), NMR ($CDCl_3$) and Mass Spectrum ($M^+$=269, EI, 70 eV) were consistent with the structure. The yield was 1.969 g (7.32 mmol, 50.03%).

Elemental Analysis

|   | Calculated | Found |
|---|------------|-------|
| C | 71.35 | 71.45 |
| H | 7.11 | 7.29 |
| N | 15.60 | 15.56 |
| O | 5.94 | |

EXAMPLE 5

3-(1-Piperazinyl)-4,5-dihydronaphth[1,2-c]isoxazole

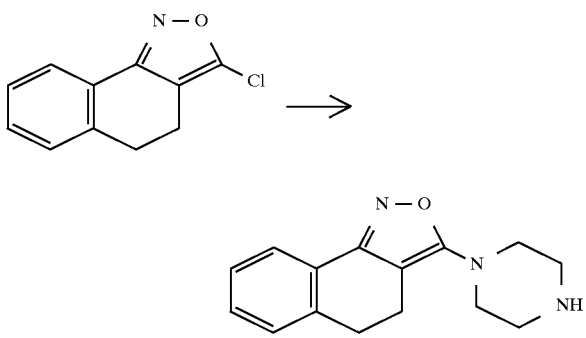

A stirred mixture of 3-chloro-4,5-dihydronaphth[1,2-c] isoxazole (5.0 g, 24.4 mmol), piperazine (34.2 g, 397.7 mmol) and $K_2CO_3$ (6.73 g, 48.7 mmol) in 40 ml of N-methylpyrrolidinone under $N_2$ was lowered into an oil bath preheated to 150° C. The mixture was heated while stirring under $N_2$ for 45 minutes. At that time, TLC ($CH_2Cl_2$) showed no remaining starting material. The mixture was removed from the heating bath, allowed to cool to room temperature and extracted with $Et_2O$. This organic phase was washed twice with $H_2O$, dried over $MgSO_4$, filtered and concentrated in vacuo to obtain a crude solid. The solid was collected, recrystallized from heptane/$Et_2O$ and dried in vacuo (0.1 mm) at 85° C. to provide pure product, mp of 97°–99° C., homogeneous by TLC [silica, 1:1 $CH_3OH$:$CH_2Cl_2$, Rf=0.35]. The IR ($CHCl_3$), NMR ($CDCl_3$) and Mass Spectrum ($M^+$=255, EI, 70 ev) were consistent with the structure. The yield was 3.372 g (13.22 mmol, 54.19%).

7

Elemental Analysis

|   | Calculated | Found |
|---|---|---|
| C | 70.56 | 70.38 |
| H | 6.71 | 6.67 |
| N | 16.46 | 16.47 |
| O | 6.27 | |

EXAMPLE 6

3-(4-Benzyl-1-piperazinyl)4,5-dihydronaphth[1,2-c]isoxazole

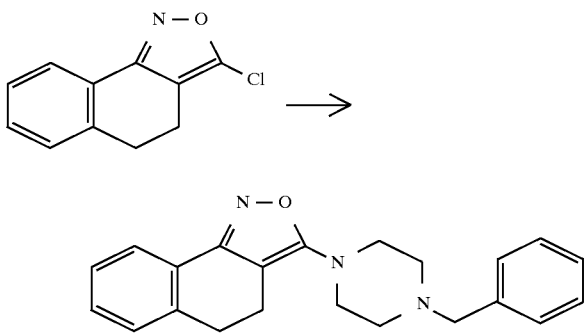

A stirred mixture of 3-chloro-4,5-dihydronaphth[1,2-c]isoxazole (2.0 g, 9.75 mmol), 1-benzylpiperazine (17 ml, 97.5 mmol) and $K_2CO_3$ (2.7 g, 19.5 mmol) in 18 ml of N-methylpyrrolidinone under $N_2$ was lowered into an oil bath preheated to 150° C. The mixture was heated while stirring under $N_2$ for 2 hours. At that time, TLC ($CH_2Cl_2$) showed no remaining starting material. The mixture was removed from the heating bath, allowed to cool to room temperature and extracted with heptane. The organic phase was dried over $MgSO_4$, filtered and concentrated in vacuo to obtain a crude solid. The solid was collected, titrated with $Et_2O$, recrystallized from $Et_2O$ and dried in vacuo (0.1 mm) at 85° C. to provide pure product, mp of 164°–166° C., homogeneous by TLC [silica, 1:1 EtOAc, Rf=0.80]. The IR ($CHCl_3$), NMR ($CDCl_3$) and Mass Spectrum ($M^+$=345, EI, 70 eV) were consistent with the structure. The yield was 1.219 g (3.53 mmol, 36.24%).

Elemental Analysis

|   | Calculated | Found |
|---|---|---|
| C | 76.49 | 76.49 |
| H | 6.71 | 6.85 |
| N | 12.16 | 12.09 |
| O | 4.63 | |

8

EXAMPLE 7

3-Hydroxy-8-methoxy-4,5-dihydronaphth[1,2-c]isoxazole

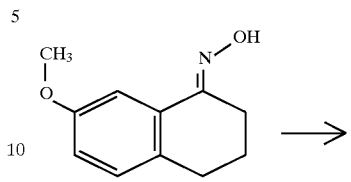

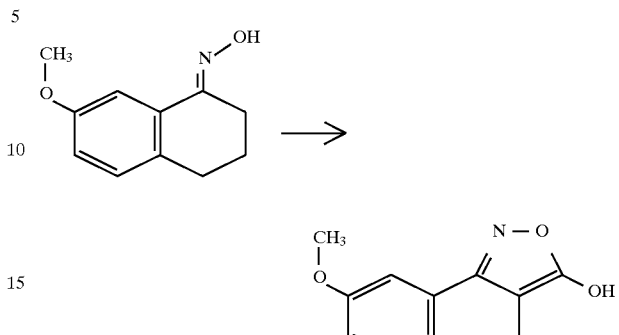

To a mechanically stirred mixture of 7-methoxy α-tetralone oxime (5.0 g, 26.18 mmol) in anhydrous THF (150 ml) at 0° C. under $N_2$ was slowly added n-butyl-lithium (n-BuLi) (23.0 ml of a 2.5M solution in hexane, 57.60 mmol). The mixture was stirred at 0° C. for 30 minutes, then $CO_2$ gas was bubbled into the solution. (As this addition progressed, a solid precipitate began to form). After 15 minutes, $CO_2$ addition was stopped and $N_2$ flow was restored. The thick mixture was stirred and warmed slowly to room temperature for 1½ hours, then 6N $H_2SO_4$ (150 ml) was slowly added which dissolved the solids. The TLC showed traces of starting oxime and a mixture of desired product and an intermediate which was not isolated. Stirring was continued for 4 hours at which time the intermediate was completely converted to product. The mixture was extracted exhaustively with EtOAc. The organic fractions were combined, washed once with $H_2O$, once with brine, dried over $MgSO_4$ and filtered. Concentration in vacuo caused the precipitation of a solid which was collected, titrated with EtOAc, and dried in vacuo to provide the product as a solid, mp of 135°–138° C., homogeneous by TLC [silica, 10:90 $CH_3OH$:EtOAc, Rf=0.46]. The IR (KBr), NMR (DMSO-$d_6$) and Mass Spectrum ($M^+$=217, EI, 70 eV) were consistent with the structure. The yield was 2.0496 g (9.45 mmol, 36.08%).

Elemental Analysis

|   | Calculated | Found |
|---|---|---|
| C | 66.35 | 66.02 |
| H | 5.10 | 5.03 |
| N | 6.45 | 6.22 |
| O | 22.10 | |

EXAMPLE 8

3-Chloro-8-methoxy-4,5-dihydronaphth[1,2-c]isoxazole

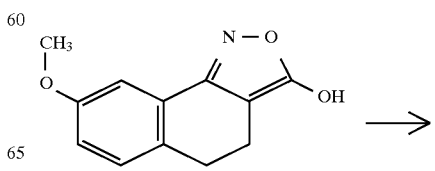

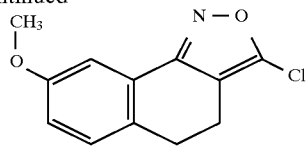

To a stirred mixture of 3-hydroxy-8-methoxy-4,5-dihydronaphth[1,2-c]isoxazole (10.0 g, 46.08 mmol) in phosphorus oxychloride (12.8 ml, 137.3 mmol), triethylamine (6.42 ml, 46.08 mmol) was added dropwise. After completion of addition, the mixture was heated to reflux while stirring. After 4 hours, no starting material remained as shown by TLC [silica, EtOAc]. The mixture was cooled to room temperature, poured into 400 ml of ice water, and extracted with heptane. The organic extracts were combined, dried over MgSO$_4$, filtered and concentrated in vacuo. Concentration of the filtrate in vacuo caused a solid to precipitate. The solid was triturated with heptane and dried in vacuo to provide the product as needles, mp of 55°–57° C., homogeneous by TLC [silica, CH$_2$Cl$_2$, Rf=0.45]. The IR (CHCl$_3$), NMR (CDCl$_3$) and Mass Spectrum (M$^+$=235, EI, 70 eV) were consistent with the structure. The yield was 7.75 g (32.98 mmol, 71.57%).

Elemental Analysis

|   | Calculated | Found |
|---|---|---|
| C | 61.16 | 61.29 |
| H | 4.28 | 4.16 |
| Cl | 15.04 |  |
| N | 5.94 | 5.90 |
| O | 13.58 |  |

EXAMPLE 9

3-[(1-Methyl-4-piperidinyl)oxy]-4,5-dihydronaphth[1,2-c]isoxazole

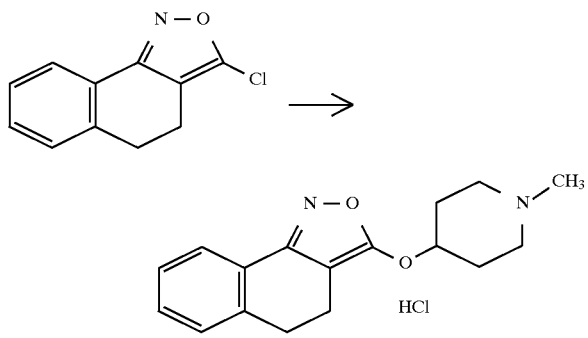

To a stirred solution mixture of 4-hydroxy-N-methyl piperidine (5.05 g, 43.89 mmol) in 100 ml of N-methylpyrrolidinone under N$_2$ was added NaH (1.75 g of a 60% dispersion in oil, 43.89 mmol). The mixture was stirred at room temperature for 15 minutes, then a solution of 3-chloro-4,5-dihydronaphth[1,2-c]isoxazole (3.0 g, 14.63 mmol) in 15 ml N-methylpyrrolidinone was added in one portion. The stirred mixture was lowered into an oil bath preheated to 150° C. After 20 minutes TLC [CH$_2$Cl$_2$] showed no starting materials remaining. The mixture was removed from the heating bath and allowed to cool to room temperature. It was then partitioned between heptane/H$_2$O. The heptane phase was washed with water, dried over MgSO$_4$, filtered and concentrated in vacuo. This crude oil obtained was taken up in Et$_2$O, filtered, and the HCl salt precipitated by the addition of ethanolic HCl. This salt was recrystallized from CH$_2$Cl$_2$/Et$_2$O to provide the product as a solid, mp of 147°–50° C., homogeneous by TLC [silica, 1:1 CH$_3$OH:EtOAc, Rf=0.02]. The IR (KBr), NMR (CDCl$_3$) and Mass Spectrum (M$^+$+1=285, CI, methane) were consistent with the structure. The yield was 1.2994 g (4.05 mmol, 36.09%).

Elemental Analysis

|   | Calculated | Found |
|---|---|---|
| C | 63.65 | 63.55 |
| H | 6.60 | 6.63 |
| Cl | 11.05 |  |
| N | 8.73 | 8.78 |
| O | 9.97 |  |

EXAMPLE 10

3-(1-Piperazinyl)-8-methoxy-4,5-dihydronaphth[1,2-c]isoxazole

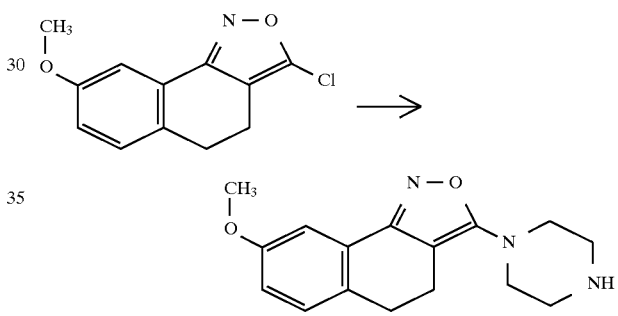

A stirred mixture of 3-chloro-8-methoxy-4,5-dihydronaphth[1,2-c]isoxazole (2.0 g, 8.51 mmol), piperazine (7.0 g, 80.6 mmol) and K$_2$CO$_3$ (2.4 g, 17.1 mmol) in 8.0 ml of N-methylpyrrolidinone under N$_2$ was lowered into an oil bath preheated to 150° C. The mixture was heated while stirring under N$_2$ for 20 minutes. At that time TLC [CH$_2$Cl$_2$] showed no starting material remained. The mixture was removed from the heating bath and allowed to cool to room temperature. Upon dilution of the reaction mixture with H$_2$O, a solid precipitated which was collected and dried in vacuo to provide pure product, mp of 86°–88° C., homogeneous by TLC [silica, 1:1 CH$_3$OH:CH$_2$Cl$_2$, Rf=0.37]. The IR (CHCl$_3$), NMR (CDCl$_3$) and Mass Spectrum (M$^+$=285, EI, 70 eV) were consistent with the structure. The yield was 1.932 g (6.78 mmol, 79.66%).

Elemental Analysis

|   | Calculated | Found |
|---|---|---|
| C | 67.35 | 66.99 |
| H | 6.71 | 6.77 |
| N | 14.73 | 14.53 |
| O | 11.21 |  |

EXAMPLE 11

3-(1-Homopiperazinyl)-8-methoxy-4,5-dihydronaphth[1,2-c]isoxazole

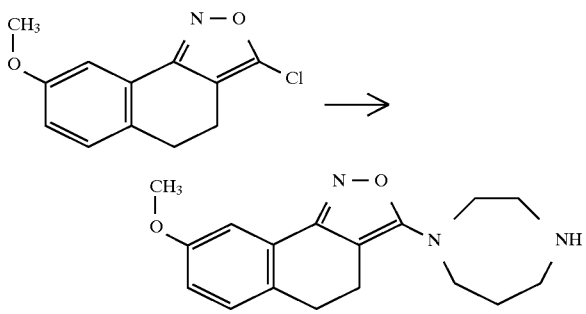

A stirred mixture of 3-chloro-8-methoxy-4,5-dihydronaphth[1,2-c]isoxazole (2.66 g, 11.32 mmol), homopiperazine (11.40 g, 113.2 mol) and $K_2CO_3$ (3.13 g, 22.68 mmol) in 10.0 ml of N-methylpyrrolidinone under $N_2$ was lowered into an oil bath preheated to 150° C. The mixture was heated while stirring under $N_2$ for 20 minutes. At that time, TLC ($CH_2Cl_2$) showed no starting material remained. The mixture was removed from the heating bath, allowed to cool to room temperature and diluted with $H_2O$, which caused a solid to precipitate. The crude solid was dried, recrystallized from $Et_2O$ and dried in vacuo (0.1 mm) at 85° C., to provide pure product, mp of 106°–109° C., homogeneous by TLC [silica, 1:1 $CH_3OH$:$CH_2Cl_2$, Rf=0.18]. The IR ($CHCl_3$), NMR ($CDCl_3$) and Mass Spectrum ($M^+$=299, EI, 70 eV) were consistent with the structure. The yield was 1.7948 g (6.00 mmol, 53.03%).

Elemental Analysis

|   | Calculated | Found |
|---|---|---|
| C | 68.21 | 68.24 |
| H | 7.07 | 7.11 |
| N | 14.04 | 14.00 |
| O | 10.69 | |

EXAMPLE 12

3-(1-(4-(p-Chlorophenyl)-4-hydroxy-piperidinyl)-8-methoxy-4,5-dihydronaphth[1,2-c]isoxazole

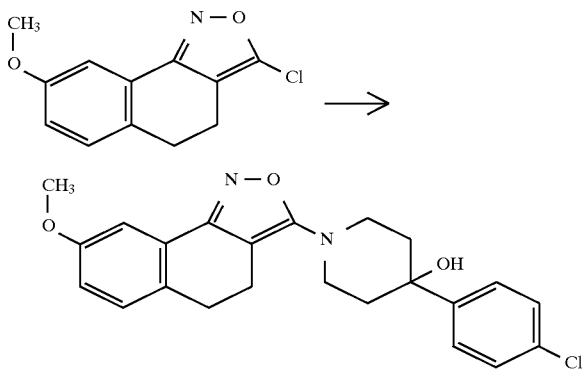

A stirred mixture of 3-chloro-8-methoxy-4,5-dihydronaphth[1,2-c]isoxazole (2.0 g, 8.51 mmol), 4-(p-chlorophenyl)-4-hydroxy-dipiperidine (3.6 g, 17.02 mol) and $K_2CO_3$ (2.35 g, 17.02 mmol) in 6 ml of N-methylpyrrolidinone under $N_2$ was lowered into an oil bath preheated to 150° C. The mixture was heated while stirring under $N_2$ for 1 hour. At that time, TLC [$CH_2Cl_2$] showed no remaining starting material. The mixture was removed from the heating bath and allowed to cool to room temperature. Upon dilution of the reaction mixture with $H_2O$, a solid precipitated which was recrystallized from EtOAc and dried in vacuo (0.1 mm) at 85° C. to provide pure product, mp of 174°–177° C., homogeneous by TLC [silica, 2:1 heptane:EtOAc, Rf=0.263]. The IR ($CHCl_3$), NMR ($CDCl_3$) and Mass Spectrum ($M^+$=410, E.I., 70 eV) were consistent with the structure. The yield was 2.3798 g (5.60 mmol, 68.20%).

Elemental Analysis

|   | Calculated | Found |
|---|---|---|
| C | 67.23 | 67.24 |
| H | 5.64 | 5.75 |
| Cl | 8.63 | |
| N | 6.82 | 8.78 |
| O | 11.68 | |

EXAMPLE 13

3-[(endo)-8-Methyl-8-azabicyclo[3.2.1]oct-3-yl)oxy]-8-methoxy-4,5-dihydronaphth[1,2-c]isoxazole

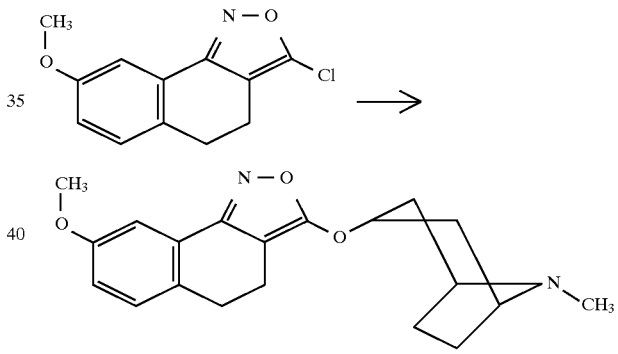

To a stirred mixture of tropine (5.41 g, 38.31 mmol) in 10 ml of (THF) under $N_2$ at 0° C. was slowly added n-BuLi (15.0 ml of a 2.5M solution in hexanes, 38.31 mmol). The mixture was stirred for 15 minutes while allowed to warm to room temperature, then a solution of 3-chloro-8-methoxy-4,5-dihydronaphth[1,2-c]isoxazole (3.0 g, 12.76 mmol) in 30 ml N-methylpyrrolidinone was added in one portion. The internal temperature increased to 99°–100° C. and was maintained there. After 3 hours, TLC [$CH_2Cl_2$] showed no starting material remaining. The mixture was removed from the heating bath and allowed to cool to room temperature. It was then partitioned between heptane/$H_2O$. The heptane phase was washed with $H_2O$, dried over $MgSO_4$, filtered and concentrated in vacuo, whereupon it solidified. This crude solid was recrystallized from a minimum of heptane and dried in vacuo to provide the product as a solid, mp of 102°–104° C., homogeneous by TLC [silica, 1:1 $CH_3OH$:$CH_2Cl_2$, Rf=0.20]. The IR ($CHCl_3$), NMR ($CDCl_3$) and Mass Spectrum ($M^+$=341, CI, methane) were consistent with the structure. The yield was 1.3729 g (4.038 mmol, 31.64%).

Elemental Analysis

|   | Calculated | Found |
|---|---|---|
| C | 70.57 | 70.47 |
| H | 7.11 | 7.25 |
| N | 8.23 | 8.14 |
| O | 14.10 | |

EXAMPLE 14

3-[(endo-8-Methyl-8-azabicyclo[3.2.1]oct-3-yl)oxy]-4,5-dihydronaphth[1,2-c]isoxazole hydrochloride hemihydrate

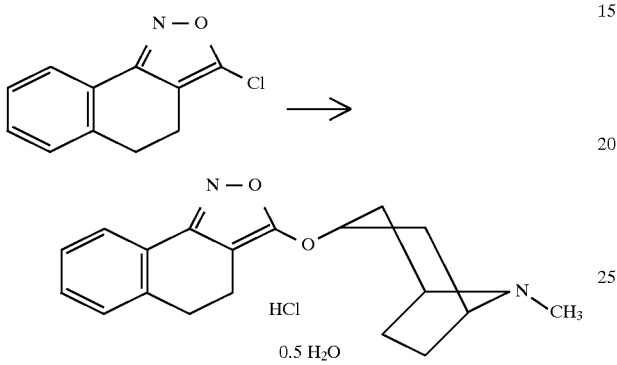

To a stirred mixture of tropine (4.4 g, 31.16 mmol) in 10 ml of THF under $N_2$ at 0° C. was slowly added n-BuLi (12.47 ml of a 2.5M solution in hexanes, 31.16 mmol). The mixture was stirred for 15 minutes while allowed to warm to room temperature, then a solution of 3-chloro-4,5-dihydronaphth[1,2-c]isoxazole (2.13 g, 10.39 mmol) in 30 ml N-methylpyrrolidinone was added in one portion. The stirred mixture was lowered into an oil bath preheated to 150° C. The internal temperature increased to 85° C. and was maintained there. After 3 hours, TLC [$CH_2Cl_2$] showed no remaining starting material. The mixture was removed from the heating bath and allowed to cool to room temperature. It was then partitioned between heptane/$H_2O$. The heptane phase was washed with $H_2O$, dried over $MgSO_4$, filtered and concentrated in vacuo, to provide the free base as an oil, which resisted is attempts at crystallization. The oil was taken up in $Et_2O$ and the HCl salt was precipitated by the addition of ethanolic HCl. This crude solid was recrystallized from $Et_2O/CH_2Cl_2$ and dried in vacuo at 85° C. to provide the product as a solid, mp of 167°–170° C., (darkens at ca. 150° C.) homogeneous by TLC [silicia, 1:1 $CH_3OH:CH_2Cl_2$, Rf=0.14]. The IR ($CHCl_3$), NMR ($CDCl_3$) and Mass Spectrum ($M^++1=311$, CI, methane) were consistent with the structure. Analysis and NMR confirmed the hemihydrate structure. The yield was 1.268 g (3.563 mmol, 34.29%).

Elemental Analysis

|   | Calculated | Found |
|---|---|---|
| C | 64.12 | 64.25 |
| H | 6.80 | 6.77 |
| Cl | | |
| N | 7.87 | 7.70 |
| O | 9.23 | |

EXAMPLE 15

3-(1-(4-(6-Fluorobenzisoxazol-3-yl)-piperidinyl)-8-methoxy-4,5-dihydronaphth[1,2-c]isoxazole

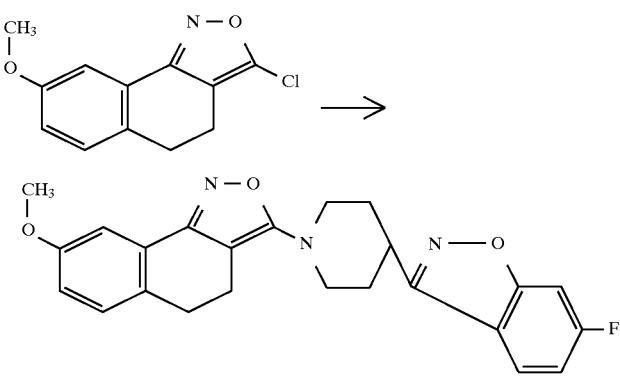

A stirred mixture of 3-chloro-8-methoxy-4,5-dihydronaphth[1,2-c]isoxazole (2.0 g, 8.51 mmol), 4-(6-fluorobenzisoxazol-3-yl)-piperidine (2.8 g, 12.76 mmol) and $K_2CO_3$ (2.35 g, 17.02 mmol) in 10 ml of N-methylpyrrolidinone under $N_2$ was lowered into an oil bath preheated to 150° C. The mixture was heated while stirring under $N_2$ for 90 minutes. At that time TLC ($CH_2Cl_2$) showed no remaining starting material. The mixture was removed from the heating bath and allowed to cool to room temperature. Upon dilution of the reaction mixture with $H_2O$, a solid precipitated which was collected, dried, dissolved in $CH_2Cl_2$ and filtered through neutral alumina. The fractions containing desired product were combined and concentrated, and the resultant solid obtained was triturated with $Et_2O$ to provide a solid, mp of 181°–183° C., homogeneous by TLC [silica, 2:1 Heptane:EtOAc, Rf=0.15]. The IR ($CHCl_3$), NMR ($CDCl_3$) and Mass Spectrum ($M^+=419$, EI, 70 eV) were consistent with the structure. The yield was 1.1318 g (2.70 mmol, 31.70%).

15

Elemental Analysis

|   | Calculated | Found |
|---|---|---|
| C | 68.72 | 68.47 |
| H | 5.29 | 5.28 |
| F | 4.53 | |
| N | 10.02 | 9.97 |
| O | 11.44 | |

EXAMPLE 16

3-(1-(4-2-Oxo-1-benzimidazolinyl)piperidinyl))-8-methoxy-4,5-dihydronaphth[1,2-c]isoxazole

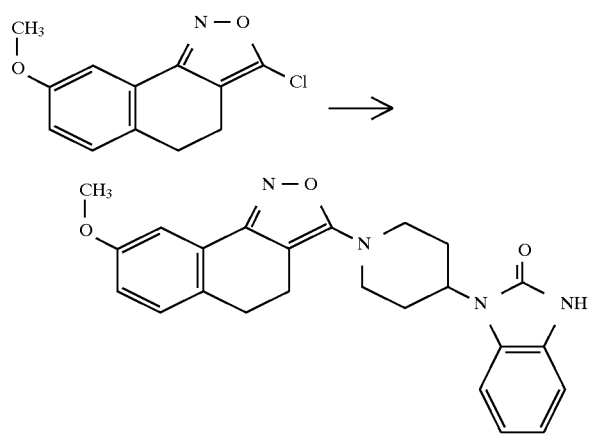

A stirred mixture of 3-chloro-8-methoxy-4,5-dihydronaphth[1,2-c]isoxazole (2.57 g, 10.9 mmol), 4-(2-oxo-1-benzimidazolinyl)piperidine (4.74 g, 21.8 mmol) and $K_2CO_3$ (3.02 g 21.8 mmol) in 12 ml of N-methylpyrrolidinone under $N_2$ was lowered into an oil bath preheated to 150° C. The mixture was heated while stirring under $N_2$ for 4 hours. At that time, TLC ($CH_2Cl_2$) showed no remaining starting material. The mixture was removed from the heating bath and allowed to cool to room temperature. Upon dilution of the reaction mixture with $H_2O$, a solid precipitated which was collected, dried, dissolved in $CH_2Cl_2$ and filtered through neutral alumina using $CH_2Cl_2$ and then 1:1 $CH_2Cl_2$:$Et_2O$. The fractions containing desired product were combined and concentrated, and the resultant solid obtained was triturated with EtOAc and dried in vacuo (0.1 mm Hg, 85° C. to provide a solid, mp of 211°–214° C., homogeneous by TLC [silica, EtQAc, Rf=0.38]. The IR ($CHCl_3$), NMR ($CDCl_3$) and Mass Spectrum ($M^+$=416, EI, 70 eV) were consistent with the structure. The yield was 1.602 g (3.85 mmol, 33.33%).

Elemental Analysis

|   | Calculated | Found |
|---|---|---|
| C | 69.21 | 68.88 |
| H | 5.81 | 5.90 |
| N | 13.45 | 13.10 |
| O | 11.52 | |

EXAMPLE 17

3-[(Quinuclidin-3-yl)oxy]-8-methoxy-4,5-dihydronaphth[1,2-c]isoxazole hydrochloride

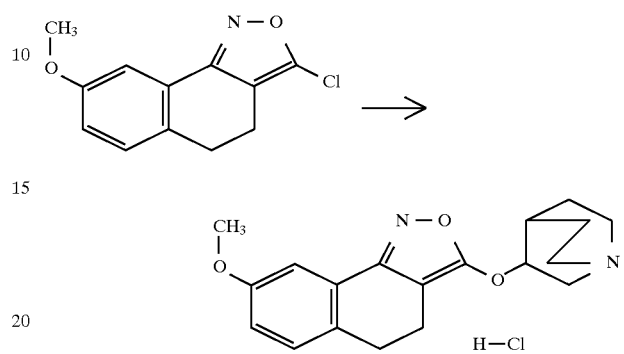

To a stirred mixture of 3-quinuclidinol (4.87 g, 38.28 mmol) in 10 ml of THF under $N_2$ at 0° C. was slowly added n-BuLi (15.32 g of a 2.5M solution in hexanes, 38.28 mmol). The mixture was stirred for 10 minutes while allowing to warm to room temperature, then a solution of 3-chloro-8-methoxy-4,5-dihydronaphth[1,2-c]isoxazole (3.0 g, 12.76 mmol) in 30 ml N-methylpyrrolidinone was added in one portion. The stirred mixture was lowered into an oil bath preheated to 150° C. The internal temperature increased to 85° C. and was maintained there. After 3 hours, TLC [$CH_2Cl_2$] showed no remaining starting material. The mixture was removed from the heating bath and allowed to cool to room temperature. It was then partitioned between heptane/$H_2O$. The heptane phase was dried over $MgSO_4$, filtered and concentrated in vacuo to provide the free base as an oil. The oil was taken up in $Et_2O$ and the HCl salt was precipitated by the addition of ethanolic HCl. This solid was collected and dried in vacuo (0.1 mm Hg, 85° C.) to provide the product as a solid, mp of 133°–136° C., homogeneous by TLC [silica, 1:1 $CH_3OH$:$CH_2Cl_2$, Rf=0.23]. The IR (KBr), NMR (DMSO-$d_6$) and Mass Spectrum ($M^+$+1=326, EI, 70 eV) were consistent with the structure. The yield was 0.965 g (2.39 mmol, 18.79%).

Elemental Analysis

|   | Calculated | Found |
|---|---|---|
| C | 62.89 | 62.91 |
| H | 6.39 | 6.28 |
| Cl | 9.77 | |
| N | 7.72 | 7.51 |
| O | 13.23 | |

EXAMPLE 18

5,6-Dihydro-4H-benzo[6,7]cyclohept[1,2-c]isoxazol-3-ol

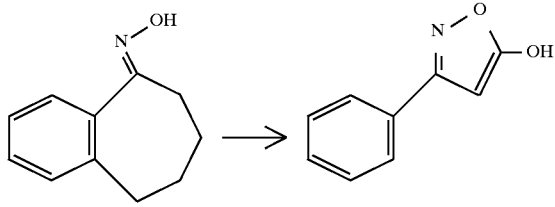

To a mechanically-stirred mixture of 1-benzosuberone oxime (10.0 g, 57.1 mmol) in anhydrous THF (200 ml) at 0° C. under $N_2$ was slowly added n-BuLi (50.3 ml of a 2.5M solution in hexane, 125.62 mmol). The mixture was stirred at 0° C. for 30 minutes, then $CO_2$ gas was bubbled into the solution. After 15 minutes, $CO_2$ addition was stopped and $N_2$ flow was restored. The thick mixture was stirred and warmed slowly to room temperature for 1½ hours, then 6N $H_2SO_4$ (220 ml) was slowly added, which dissolved the solids. Stirring was continued for 18 hours, at which time the TLC [EtOAc] showed a mixture of starting oxime and product (starting oxime was best visualized using 2:1 heptane:EtOAc eluent). The mixture was poured into a separatory funnel, and the organic phase drawn off. The aqueous phase was extracted with EtOAc, and the organic phase and the EtOAc extracts were combined, washed with $H_2O$, dried over $MgSO_4$ and filtered. Concentration in vacuo caused the precipitation of a solid which was collected and dried in vacuo to provide the product as a solid, mp of 165°–168° C., homogeneous by TLC [silica, $Et_2O$, Rf=0.28]. The IR (KBr), NMR (DMSO-$d_6$) and Mass Spectrum ($M^+$=201, EI, 70 eV) were consistent with the structure. The yield was 3.0324 g (15.09 mmol, 26.42%).

Elemental Analysis

|   | Calculated | Found |
|---|---|---|
| C | 71.63 | 71.45 |
| H | 5.51 | 5.50 |
| N | 6.96 | 6.91 |
| O | 15.90 |  |

EXAMPLE 19

3-(1-(4-(2-Oxo-1-benzimidazolinyl)piperidinyl))-4,5-dihydronaphth[1,2-c]isoxazole hemihydrate

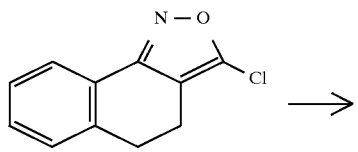

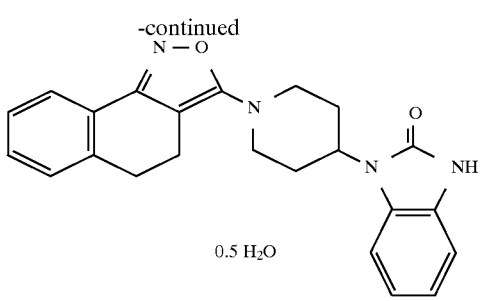

A stirred mixture of 3-chloro-4,5-dihydronaphth[1,2-c]isoxazole (3.1 g, 15.12 mmol), 4-(2-oxo-1-benzimidazolinyl)-piperidine (8.2 g, 37.8 mmol) and $K_2CO_3$ (4.2 g, 30.24 mmol) in 18 ml of N-methylpyrrolidinone under $N_2$ was lowered into an oil bath preheated to 150° C. The mixture was heated while stirring under $N_2$ for 90 minutes. At that time, TLC ($CH_2Cl_2$) showed no remaining starting material. The mixture was removed from the heating bath and allowed to cool to room temperature. Upon dilution of the reaction mixture with $H_2O$, a solid precipitated which was collected, dried, dissolved in $CH_2Cl_2$ and filtered through neutral alumina using $CH_2Cl_2$ and then 1:1 $CH_2Cl_2$:$Et_2O$. The fractions containing desired product were combined and concentrated, and the solid obtained was recrystallized from EtOAc and dried in vacuo (0.1 mm Hg, 110° C.) to provide a solid, mp of 229°–233° C., homogeneous by TLC [silica, EtOAc, Rf=0.54]. The IR (KBr), NMR ($CDCl_3$) and Mass Spectrum ($M^+$=386, EI, 70 eV) were consistent with the structure. Analysis and NMR confirmed a hemihydrate structure. The yield was 1.103 g (2.79 mmol, 18.45%).

Elemental Analysis

|   | Calculated | Found |
|---|---|---|
| C | 69.82 | 70.25 |
| H | 5.86 | 5.64 |
| N | 14.17 | 14.22 |
| O | 8.28 |  |

Preferred pharmaceutically acceptable addition salts include salts of inorganic acids such as hydrochloric, hydrobromic, sulfuric, nitric, phosphoric and perchloric acids; as well as organic acids such as tartaric, citric, acetic, succinic, maleic, fumaric, and oxalic acids.

The active compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, waters, chewing gums and the like. These preparations should contain or form at least 0.5% of active compound, but may be varied depending upon the particular form and may conveniently be from about 4 to about 75% of the weight of the unit. The amount of compound present in such composition is such that a suitable dosage of active compound will be obtained. Preferred compositions and preparations according to the present invention are prepared so that an oral dosage unit form contains from about 1.0 to about 300 mgs of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel™, corn starch and the like; a lubricant such as magnesium stearate or Sterotex®; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings an flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of the aforesaid compound, but may be varied from about 0.5 to about 30% of the weight thereof. The amount of compound in such composition is such that a suitable dosage of active compound will be obtained. Preferred compositions and preparations according to the invention are prepared so that a parenteral dosage unit contains from about 0.5 to about 100 mgs of active compound.

The solutions or suspensions may also include the following components; a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates and agents for the adjustment of tonicity such as sodium chloride or dextrose. The parenteral preparation can be enclosed in ampules, disposable syringes or multiple dose vials made of glass or plastic.

The compounds of the invention may be useful as 5-$HT_3$ antagonists on the coronary chemoreflex for the treatment of anxiety, psychiatric disorders, nausea and vomiting by virtue of their ability to bind to rat entorhinal cortex membranes.

$^3$H-GR 65630 Binding to Rat Entorhinal Cortex Membranes

Studies have been performed to determine the affinity of the compounds of the invention for the $5HT_3$ binding site in the brain. This study or assay may be useful for predicting the potential of compounds to exhibit antiemetic, anxiolytic or atypical antipsychotic profiles.

Originally, it was believed that $5HT_3$ binding sites existed only in the periphery. However, with the recent introduction of potent and selective $5HT_3$ antagonist drugs such as GR65630, Zacopride, ICS 205 930 and MDL 72222 (Bemesetron, $C_{15}H_{17}Cl_2NO_2$), data from binding studies have indicated that $5HT_3$ binding sites are also located in selected areas of the brain. The highest levels of $5HT_3$ binding sites have been detected in limbic and dopamine containing brain areas (entorhinal cortex, amygdala, nucleus accumbens and tuberculum olfactorium) (Kilpatrick, G. J. et al. Identification and distribution of $5HT_3$ receptors in rat brain using radioligand binding. Nature 330: 746–748). Besides possessing selective binding in dopamine rich areas, $5HT_3$ antagonists have been reported to block behavioral effects associated with certain drugs of abuse (nicotine and morphine) and to be active in behavioral tests predictive of anxiolytic activity. Based on these selective regional binding results and behavioral studies, $5HT_3$ antagonists may have a therapeutic benefit in disease states believed to be associated with excessive dopaminergic activity, i.e., schizophrenia, anxiety and drug abuse.

In accordance with the above-discussed assay, a 0.05M of Krebs-Hepes buffer, pH 7.4 was prepared as follows:

| | |
|---|---|
| 11.92 g | Hepes |
| 10.52 g | NaCl |
| 0.373 g | KCl |
| 0.277 g | $CaCl_2$ |
| 0.244 g | $MgCl_2.6H_2O$ | q.s. to 1 liter with distilled $H_2O$, bring pH up to 7.4 (at 4° C.) with 5N NaOH

[$^3$H]-GR65630 (87.0 Ci/mmol) was obtained from New England Nuclear. For $IC_{50}$ determinations: [$^3$H]-GR65630 was made up to a concentration of 1.0 nM in Krebs-Hepes buffer such that when 100 μl is added to each tube, a final concentration of 0.4 nM is attained in the 250 μl assay.

GR38032F was obtained from Research Biochemical Inc. GR38032F was made up to a concentration of 500 μM in Krebs-Hepes buffer. 50 μl of Krebs-Hepes were added to each of 3 tubes for determination of nonspecific binding (yields a final concentration of 100 μM in the 250 μl assay).

For most assays, a 50 μM stock solution was prepared in a suitable solvent and serially diluted with Krebs-Hepes buffer such that when 50 μl of drug is combined with the total 250 μl assay, a final concentration from $10^{-5}$ to $10^{-8}$M was attained. Characteristically, seven concentrations may be used for each assay; however, higher or lower concentrations may be used, depending on the potency of the drug.

During tissue preparation, Male Wistar rats (15–200 g) were decapitated, the entorhinal cortex removed, weighed and homogenized in 10 volumes of ice cold 0.05M Krebs-Hepes buffer, pH 7.4. The homogenate is centrifuged at 48,000 g for 15 minutes at 4° C. The resulting pellet was rehomogenized in fresh Krebs-Hepes buffer and recentrifuged at 48,000 g for 15 minutes at 4° C. The final pellet was resuspended in the original volume of ice-cold Krebs-Hepes buffer. This yielded a final tissue concentration of 1.2 to 1.6 mg/ml with the addition of 100 μl to the assay. Specific binding was approximately 55 to 65% of the total bound ligand.

In conducting the assay, the following volumes were utilized:

| | |
|---|---|
| 100 μl | of Tissue suspension; |
| 100 μl | of [$^3$H]-GR65630; and |
| 50 μl | 500M GR38032F (Vehicle for binding) or appropriate drug concentration |

Sample tubes were kept on ice for additions, then vortexed and incubated with continuous shaking for 30 minutes at 37° C. At the end of the incubation period, the incubate is diluted with 5 ml of ice-cold Krebs-Hepes buffer and immediately vacuum filtered through Whatman GF/B filters, followed by two 5 ml washes with ice-cold Krebes-Hepes buffer. The filters are dried and counted in 10 ml of liquid scintillation cocktail. Specific GR 65630 binding is defined as the difference between the total binding and that bound in the presence of 100 μM GR38032F. $IC_{50}$ values were derived from computer-derived log-probit analysis.

Various compounds of the invention were subjected to the above-described assay and the results the affinity for 5 HT$_3$ receptors are reported in Table I, below.

TABLE I

Affinity for 5-HT$_3$ Receptor-Displacement of $^3$H-GR 65630

| Compound | IC$_{50}$, μM |
|---|---|
| Ex. 3 | 0.868 |
| Ex. 4 | 0.083 |
| Ex. 5 | 0.056 |
| Ondansetron (stadard) | 0.089 |
| ICS 205 930 (standard) | 0.039 |

Measurement of 5 HT$_3$ Antagonist Effects in the Bezold-Jarisch Assay

This assay evaluates the effect of these compounds as 5-HT$_3$ antagonists. They were examined in this assay on the coronary chemoreflex (Bezold-Jarisch) initiated by 5-HT$_3$ in vivo and characterized by leading inhibition of sympathetic outflow and increased activity of the cardiac vagus, leading to profound bradycardia and hypotension. The values obtained allow for continuous monitoring of arterial pressure and heart rate responses by these compounds over an extended period of time to determine their effecicy for 5 HT$_3$ antagonism.

The catheters were prepared from Tygon tubing (45 cm length, 0.05 mm, ID) bonded to Teflon tubing (0.38 mm, ID). The mechanical bonding was achieved by insertion of the Teflon tubing (5 mm) into the dilated (ethylene dichloride, 3–4 min.) tip of the Tygon tubing. The junction was then sealed with vinyl glue, the catheters were soaked in cold sterilization solution (Amerse instrument germicide) and flushed thoroughly with saline prior to implantation.

Long Evans rats were anesthetized with sodium pentobarbital (50 mg/kg, ip). The catheters filled with hepranized saline (100 U/ml) were inserted in the left femoral artery and vein and passed into the abdominal aorta and inferior vena cava, respectively. The catheters were then sutured to the underlying muscle and the free ends were passed subcutaneously and exteriorized through an incision on the top of the skull. The catheters were then secured to the skin with sutures, nitrofurazone powder was dusted over the area of the incision and the incision was closed using 3-O silk sutures. The catheters were flushed with saline and sealed with metal obturators. Patentcy of the two catheters was maintained by daily flushing with hepranized saline (0.2 ml of 100 U/ml). The rats were given 48 hours recovery prior to obtaining cardiovascular data.

In the anesthetized rat model the catheters were not exteriorized, data was collected acutely under the influence of general anesthesia.

The baseline data Arterial Blood Pressure (mm Hg, systolic/diastolic) and Heart Rate (beats/min) were recorded and the rats were injected with 5-HT (3–7.5 ug/kg, iv). The individual response to the 5-HT intervention was determined and the compound was then administered singely or in an ascending dose range. The rats were challenged with 5-HT again at intervals postdosing and the peak response was recorded.

Several compounds of the invention were tested according to the above-described assay and the results are reported in Table II, below.

TABLE II

Inhibitory Potency of 5-HT$_3$ Antagonists on Reflex Bradycardia Induced by Intravenous 5-HT$_3$ in the Anesthetized Long-Evans Rat

| Compound | Dose, mg/kg, ip | % Inhibition of Bezold-Jarisch Reflex (Values are mean ± SEM, 2–3 rats/dose) |
|---|---|---|
| Ondansetron | 3.0 | 57.3 ± 9.7 |
| Ondansetron | 10.0 | 94.6 ± 2.7 |
| Ex. 4 | 0.03 | 58.6 ± 16.4 |
| Ex. 4 | 0.05 | 83.3 ± 8.2 |
| Ex. 4 | 0.10 | 93.0 ± 1.0 |
| Ex. 5 | 1.0 | 55.6 ± 9.7 |
| Ex. 5 | 3.0 | 89.3 ± 2.9 |

In accordance with Table II, maximal reductions in heart rate induced by 5HT$_3$ (e.g. Bezold-Jarisch reflex) occurred 15 to 60 minutes after administration.

I claim:

1. A compound of the formula:

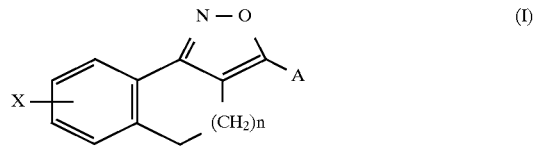

Where A is hydroxy, chloro, a group of the formula

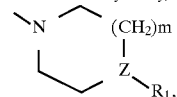

a group of the formula

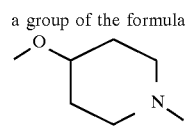

a group of the formula

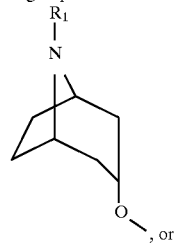

, or a group of the formula

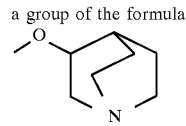

where R$_1$ is hydrogen, an alkyl group of 1 to 6 carbon atoms, optionally substituted with hydroxy, alkoxy, amino; aryl or heteroaryl, optionally substituted with halogen, hydroxy or alkoxy; or benzyl optionally substituted with halogen, hydroxy or alkoxy; n is an integer of 1 or 2; Z is N, CH or C(OH); m is an integer of 1 to 3; and X is hydrogen, hydroxy or alkoxy; the pharmaceutically acceptable salts thereof, the geometric or optional isomers thereof, or the racemic mixtures thereof, or hydrates thereof, where applicable.

2. A compound according to the claim 1, wherein A is a group of the formula

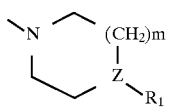

wherein $R_1$ and m are as defined above.

3. A compound according to claim 1, wherein A is a group of the formula

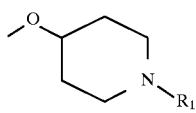

wherein $R_1$ is as defined above.

4. A compound according to claim 1, wherein A is a group of the formula

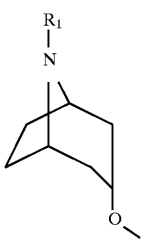

wherein $R_1$ is as defined above.

5. A compound according to claim 1, wherein A is a group of the formula

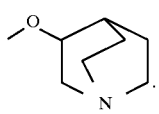

6. The compound according to claim 1, which is 3-chloro-4,5-dihydronaphth [1,2-c]isoxazole, or salts thereof.

7. The compound according to claim 1, which is 3-hydroxy-8-methoxy-4,5-dihydronaphth[1,2-c]isoxazole, or salts thereof.

8. The compound according to claim 1, which is 3-chloro-8-methoxy-4,5-dihydronaphth[1,2-c]isoxazole, or salts thereof.

9. The compound according to claim 1, which is 5,6-dihydro-4H-benzo[6,7]cyclohept[1,2-c]isoxazol-3-ol, or salts thereof.

10. The compound according to claim 2, which is 3-(4-methyl-1-piperazinyl)-4,5-dihydronaphth[1,2-c]isoxazole, or pharmaceutically acceptable salts thereof.

11. The compound according to claim 2, which is 3-(4-(2-hydroxyethyl)-1-piperazinyl)-4,5-dihydronaphth[1,2-c]isoxazole, or pharmaceutically acceptable salts thereof.

12. The compound according to claim 2, which is 3-(1-homopiperazinyl)-4,5-dihydronaphth[1,2-c]isoxazole, or pharmaceutically acceptable salts thereof.

13. The compound according to claim 2, which is 3-(1-piperazinyl)-4,5-dihydronaphth[1,2-c]isoxazole, or pharmaceutically acceptable salts thereof.

14. The compound according to claim 2, which is 3-(1-piperazinyl)-8-methoxy)-4,5-dihydronaphth[1,2-c]isoxazole, or pharmaceutically acceptable salts thereof.

15. The compound according to claim 2, which is 3-(1-hompiperazinyl)-8-methoxy)-4,5-dihydronaphth[1,2-c]isoxazole, or pharmaceutically acceptable salts thereof.

16. The compound according to claim 2, which is 3-(1-(4-(p-chlorophenyl)-4-hydroxy-piperidinyl)-8-methoxy)-4,5-dihydronaphth[1,2-c]isoxazole, or pharmaceutically acceptable salts thereof.

17. The compound according to claim 2, which is 3-(1-(4-(6-fluorobenzisoxazol-3-yl)-piperidinyl)-8-methoxy)-4,5-dihydronaphth[1,2-c]isoxazole, or pharmaceutically acceptable salts thereof.

18. The compound according to claim 2, which is 3-(1-(4-(2-oxo-1- benzimidazolynyl)piperidinyl))-8-methoxy)-4,5-dihydronaphth[1,2-c]isoxazole, or pharmaceutically acceptable salts thereof.

19. The compound according to claim 2, which is 3-(1-(4-(2-oxo-1-benzimidazolinyl)piperidinyl)) )-4,5-dihydronaphth[1,2-c]isoxazole, or pharmaceutically acceptable salts thereof.

20. The compound according to claim 3, which is 3-[(1-methyl-4-piperidinyl)oxy]-)-4,5-dihydronaphth[1,2-c]isoxazole, or pharmaceutically acceptable salts thereof.

21. The compound according to claim 4, which is 3-[(endo)-8-methyl-8-azabicyclo[3.2.1]oct-3-yl]-8-methoxy-)-4,5-dihydronaphth[1,2-c]isoxazole, the pharmaceutically acceptable salts thereof, or geometric isomers thereof.

22. The compound according to claim 4, which is 3-[(endo-8-methyl-8-azabicyclo[3.2.1.]octo-3-yl)oxy])-4,5-dihydronaphth[1,2-c]isoxazole, the pharmaceutically acceptable salts thereof, or hydrates thereof.

23. The compound according to claim 5, which is 3-[(quinuclidin-3-yl)oxy]-8-methoxy)-4,5-dihydronaphth[1,2-c]isoxazole, pharmaceutically acceptable salts thereof or optical isomers thereof, or recemic mixtures thereof.

24. A process for the preparation of a compound of the formula:

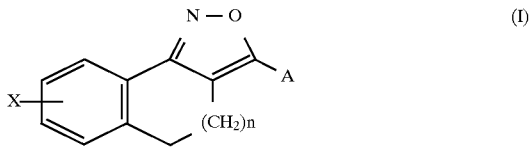

Where A is, a group of the formula

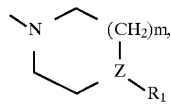

a group of the formula

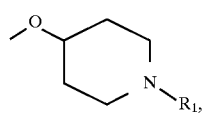

a group of the formula

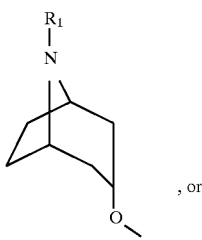

, or a group of the formula

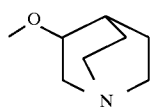

wherein $R_1$ is hydrogen, an alkyl group of 1 to 6 carbon atoms, optionally substituted with hydroxy, alkoxy, amino; aryl or heteraryl, optionally substituted with halogen, hydroxy or alkoxy; or benzyl optionally substituted with halogen, hydroxy or alkoxy; n is an integer of 1 or 2; Z is N, CH or C(OH); m is an integer of 1 to 3; and X is hydrogen, hydroxy or alkoxy, which comprises contacting a compound of the formula

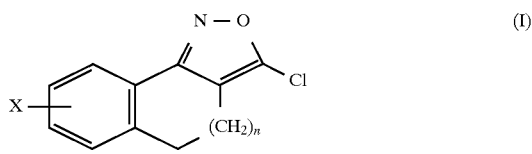 (I)

wherein X and n are as hereindefined with a compound of the formula

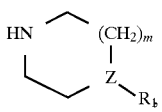

a compound of the formula

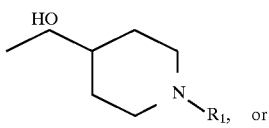, or a compound of the formula

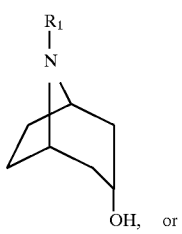, or a compound of the formula

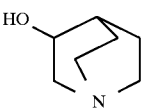

wherein $R_1$ and m are as hereindefined.

25. The process according to claim 24, wherein the method is performed in the absence of a solvent.

26. The process according to claim 25, wherein the method is performed in the presence of a solvent.

27. The process according to claim 26, wherein the solvent is N-methylpiperidine.

28. The process according to claim 27, wherein the solvent is tetrahydrofuron.

29. The process according to claim 28, wherein the solvent is hexanes.

30. The process according to claim 29, wherein a base is employed.

31. The process according to claim 27, wherein the base is potassium carbonate.

32. The process according to claim 27, wherein the base is N-butyllithium.

33. The process according to claim 27, wherein the base is sodium hydride.

34. The process according to claim 24, wherein the method is performed at a temperature from about 100° C. to about 200° C.

35. A method of reducing nausea in a mammal in need of nausea reduction which comprises administering to such a mammal a nausea reducing effective amount of a compound of claim 1.

36. A method of reducing vomiting in a mammal in need of vomiting reduction which comprises administering to such a mammal a vomiting reducing effective amount of a compound of claim 1.

37. A method of treating anxiety in a mammal in need of anxiety treatment which comprises administering, to such a mammal an anxiety treating effective amount of a compound 1.

38. A nausea reducing composition comprising an adjuvant and as the active ingredient, a nausea reducing effective amount of a compound according to claim 1.

39. A vomiting reducing composition comprising an adjuvant and as the active ingredient, a vomiting reducing effective amount of a compound according to claim 1.

40. An anxiety treating composition comprising an adjuvant and as the active ingredient, an anxiety treating effective amount of a compound according to claim 1.

41. A method of ameliorating a condition in a mammal in need of ameliorating said condition, comprising and administering a condition ameliorating effective amount of a serotonin antagonist of claim 1.

* * * * *

UNITED STATES PATENT AND TRADEMARK OFFICE
CERTIFICATE OF CORRECTION

PATENT NO. : 5,880,121
DATED : March 9, 1999
INVENTOR(S) : Nicholas J. Hrib

It is certified that error appears in the above-identified patent and that said Letters Patent is hereby corrected as shown below:

Column 25,
Lines 46 to 53, "a compound of the formula
"                                                                  "

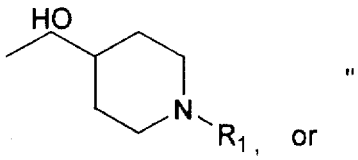

Should read -- - a compound of the formula

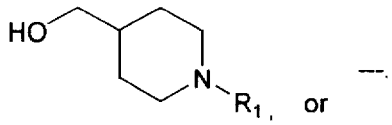

Column 26,
Lines 12 and 13, "The process according to claim 25 wherein the method is performed in the presence of a solvent." should read -- The process according to claim 24 wherein the method is performed in the presence of a solvent --.
Lines 17, and 18, "28. The process according to claim 27, wherein the solvent is tetrahydrofuron.", should read -- 28. The process according to claim 26, wherein the solvent is tetrahydrofuron --.
Lines 19 and 20, "29. The process according to claim 28, wherein the solvent is hexanes.", should read -- 29. The process according to claim 26, wherein the solvent is hexanes --.
Lines 22 and 23, "30. The process according to claim 29, wherein a base is employed." should read -- 30. The process according to claim 24, wherein a base is employed --.
Lines 24 and 25, "31. The process according to claim 27, wherein the base is potassium carbonate.", should read -- 31. The process according to claim 30, wherein the base is potassium carbonate --.
Lines 27 and 28, "32. The process according to claim 27, wherein the base is N-butyllithium.", should read -- 32. The process according to claim 30, wherein the base is N-butyllithium --.

UNITED STATES PATENT AND TRADEMARK OFFICE
CERTIFICATE OF CORRECTION

PATENT NO. : 5,880,121
DATED : March 9, 1999
INVENTOR(S) : Nicholas J. Hrib

It is certified that error appears in the above-identified patent and that said Letters Patent is hereby corrected as shown below:

Column 26,
Lines 29 and 30, "33. The process according to claim 27, wherein the base is sodium hydride.", should read -- 33. The process according to claim 30, wherein the base is sodium hydride --.

Signed and Sealed this

Twelfth Day of February, 2002

Attest:

*Attesting Officer*

JAMES E. ROGAN
*Director of the United States Patent and Trademark Office*